(12) United States Patent
Toyokawa et al.

(10) Patent No.: US 6,482,180 B2
(45) Date of Patent: Nov. 19, 2002

(54) INTRAVASCULAR CATHETER

(75) Inventors: Yoshihide Toyokawa, Yamanashi (JP);
Kenji Ishikawa, Kanagawa (JP);
Toshiya Asai, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 5 days.

(21) Appl. No.: 09/776,923

(22) Filed: Feb. 6, 2001

(65) Prior Publication Data

US 2001/0014787 A1 Aug. 16, 2001

(30) Foreign Application Priority Data

Feb. 16, 2000 (JP) .................................. 2000-038725

(51) Int. Cl.⁷ ............................................... A61M 5/00
(52) U.S. Cl. ................................................ 604/165.03
(58) Field of Search ..................................... 604/165.03

(56) References Cited

U.S. PATENT DOCUMENTS

| | | |
|---|---|---|
| 3,856,010 A | 12/1974 | Moorehead et al. |
| 4,198,973 A | 4/1980 | Millet |
| 4,687,176 A | 8/1987 | Olsen |
| 4,834,719 A | 5/1989 | Arenas |
| 5,108,374 A | 4/1992 | Lemieux |
| 5,167,635 A | 12/1992 | Haber et al. |
| 5,270,003 A | 12/1993 | Bernes et al. |
| 5,354,281 A * | 10/1994 | Chen ..................... 604/165.03 |
| 5,429,616 A | 7/1995 | Schaffer |
| 5,498,241 A * | 3/1996 | Fabozzi ................. 604/165.03 |
| 5,542,933 A | 8/1996 | Marks |
| 5,674,201 A * | 10/1997 | Steinman ............... 604/165.03 |
| 5,676,656 A * | 10/1997 | Brimball ............... 604/165.03 |
| 5,749,859 A | 5/1998 | Powell |

FOREIGN PATENT DOCUMENTS

| | | |
|---|---|---|
| EP | 0 312 073 A2 | 4/1989 |
| EP | 0 691 139 A1 | 1/1996 |
| JP | 61-25490 | 7/1986 |
| JP | 1-15308 | 3/1989 |
| JP | 6-39724 | 10/1994 |
| JP | 8-141078 | 6/1996 |
| JP | 9-509075 | 9/1997 |

* cited by examiner

Primary Examiner—Philippe Derakshani
(74) Attorney, Agent, or Firm—Burns, Doane, Swecker & Mathis, LLP (57) ABSTRACT

The present invention provides an intravascular catheter comprising a catheter part; an internal needle disposed through the catheter part; and a flexible resin member disposed on the outer surface of the catheter part. It is preferable that the intravascular catheter comprises a blood leakage prevention member for preventing leakage of blood by closing the catheter part via the flexible resin member. It is also preferable that the blood leakage prevention member comprises a pressure part capable of pressuring the catheter part via the flexible resin member. It is further preferable that the blood leakage prevention member comprises a fixing mechanism capable of fixing the pressure part in the pressuring state, and a releasing mechanism capable of releasing the pressuring state.

12 Claims, 13 Drawing Sheets

INTRAVASCULAR CATHETER

BACKGROUND OF THE INVENTION

1. Field of the Invention

The present invention relates to an intravascular catheter provided with a function for controlling the blood flow.

2. Description of the Related Art

Figure 25:
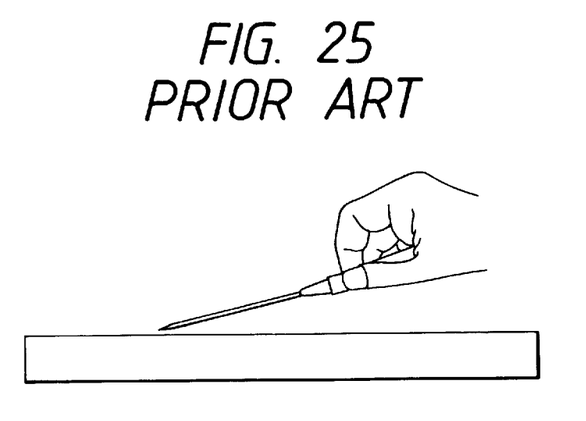
FIG. 25 is a diagram showing the operation state at the time of piercing a conventional intravascular catheter into the skin.
Figure 26:
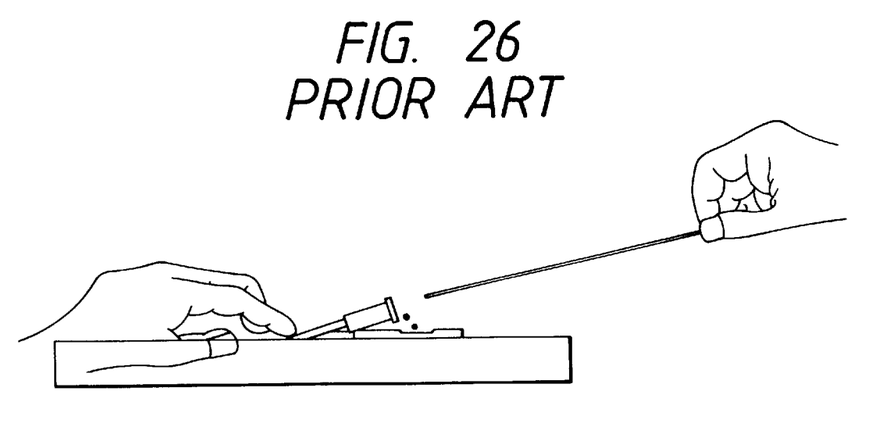
FIG. 26 is a diagram showing the state of restraining blood leakage by pressuring the catheter base end part by one finger after taking out the internal needle after piercing the intravascular catheter into the skin.

Insertion of an intravascular catheter in a blood vessel can be confirmed by flashback, that is, the backward flow of the blood at the time of piercing the intravascular catheter into the blood vessel. However, a problem of leakage of the blood flowing backward arises at the time of pulling out the internal needle. In order to cope with the problem, conventionally, a method of stopping the blood by pressing the tip end part or the hub base part of the intravascular catheter, a method of preventing the blood leakage by providing an elastic tube at the catheter base end part and pressing the tube part with a finger at the time of pulling out the internal needle, and a method of preventing blood leakage by storing an elastic tube with a swelling in the catheter base end part and pressing the swelling part (U.S. Pat. No. 3,856,010) have been proposed. FIGS. 25 and 26, show the conventional method of restraining the leakage by directly pressuring the catheter part outer surface in the vicinity of the hub base of the intravascular needle with a finger. However, since the method of directly pressuring the catheter outer surface is a method of closing the catheter itself by flattening the same with the pressure, there is a risk of breaking the catheter itself by the flattening operation so as to lead to cut-off of the catheter. Moreover, intravascular catheters comprising a means for directly pressing and closing the catheter base end part outer surface (U.S. Pat. Nos. 5,108,374 and 5,542,933) have been proposed, but since the catheter part is pressured directly in these methods, catheter breakage may be brought about.

Furthermore, since the above-mentioned methods involve the pressure from above so as to apply the pressuring force to the vicinity of the insertion part, the blood vessel, and the skin of the patient, a problem is involved in that the patient suffers the great pain.

As a means for preventing the blood leakage without giving a pain to the patient, a method of providing a blood flow controlling device such as a check valve, a detent plug, and forceps stoppage in an elastic tube part can be presented. Examples of the methods include a method of further providing an elastic clamp tube part between a hub part at the catheter base end part and a connector part as a part for connecting with an external circuit so as to enable closure with forceps (JP-B-61-25490U, JP-B-6-39724U). However, in the case of using a tool such as metal forceps, since the elastic clamp tube is fixed firmly by clamping, there is a risk of ruining the elastic clamp tube part to cause breakage as in the above-mentioned methods so as to lead to leakage of the blood or the transfusion liquid. Moreover, since the forceps are bulky, the hand can be uncertain so that the safe and certain operation may be prevented. Furthermore, there is a risk of fall-off of the inserted catheter due to self weight of the forceps when the operator leaves the hand. Moreover, since the method requires the elastic clamp tube part between the hub part and the connector part, the number of parts is increased so that the production and assembly is complicated as well as the equipment cost is increased as well. Furthermore, since the length of the hub part and the connector part is prolonged for the clamp tube, a problem is involved in that the operativity and the handling convenience are deteriorated due to the bulkiness.

As a means for preventing the blood leakage without using forceps, a method of providing wing parts between the hub and the connector, and nipping the wings of both sides so as to pressure and close the elastic tube (JP-B-1-15308, JP-A8-141078, JP-W-9-509075) has been proposed. However, also in the method, the problems are not solved such as increase in the number of parts due to necessity of the elastic tube part between the hub part and the connector part, complication of the production and assembly so as to increase the equipment cost, and prolongation of the hub part and the connector part so as to cause bulkiness and operation difficulty.

As another problem, since the method of pressuring the catheter part with a finger, and the method of pressuring and closing by wings require the holding or nipping operation with one hand for fixing and maintaining the pressured state, there is a risk of inadvertent piercing by the internal needle after pulling off, or connection mistake at the time of connecting the circuit due to insufficient attentiveness.

SUMMARY OF THE INVENTION

In view of the above-mentioned circumstances, an object of the invention is to provide an intravascular catheter capable of closing the catheter part without breaking the catheter part by pressuring the catheter part via a flexible resin member provided on the outer surface of a catheter part, and further comprising a blood leakage prevention member capable of preventing the blood leakage.

Moreover, another object is to provide an intravascular catheter comprising a mechanism for easily fixing or releasing the state with the blood leakage prevented by pressuring and closing the catheter.

The invention can be realized by the following means.

A first aspect is an intravascular catheter comprising a catheter part; an internal needle disposed through the catheter part; and a flexible resin member disposed on the outer surface of the catheter part.

A second aspect is the intravascular catheter according to the first aspect, comprising a blood leakage prevention member for preventing leakage of blood by closing the catheter part via the flexible resin member.

A third aspect is the intravascular catheter according to the second aspect, wherein the blood leakage prevention member comprises a pressure part capable of pressuring the catheter part via the flexible resin member.

A fourth aspect is the intravascular catheter according to the third aspect, wherein the blood leakage prevention member comprises a fixing mechanism capable of fixing the pressure part in the pressuring state.

A fifth aspect is the intravascular catheter according to the fourth aspect, wherein the blood leakage prevention member comprises a releasing mechanism capable of releasing the pressuring state of the pressure part.

A sixth aspect is the intravascular catheter according to the second aspect, wherein the blood leakage prevention member comprises wing parts disposed on the right and left sides with respect to the axial direction of the catheter part.

A seventh aspect is the intravascular catheter according to the sixth aspect, wherein the wing parts are provided integrally with at least one of a pressure part capable of pressuring the catheter part via the flexible resin member, a fixing mechanism capable of fixing the pressure part in the pressuring state, and a releasing mechanism capable of releasing the pressuring state of the pressure part.

An eighth aspect is the intravascular catheter according to the seventh aspect, wherein the fixing mechanism is a nail part provided on at least one of the right and left wings, to be fixed by engagement with the other side wing part.

A ninth aspect is the intravascular catheter according to the seventh aspect, wherein the fixing mechanism is a nail part provided on at least one of the right and left wings, and the fixed state by engagement with the other side wing part is capable of being released.

A tenth aspect is the intravascular catheter according to the seventh aspect, wherein the fixing mechanism is a pair of projection and recess fitting parts provided each on the right and left wings, to be fixed by engagement of the projection and recess of the fitting parts.

An eleventh aspect is the intravascular catheter according to the seventh aspect, wherein the fixing mechanism achieves fixation according to engagement of the right and left wings such that one of them covers the other.

A twelfth aspect is the intravascular catheter according to the eleventh aspect, wherein the fixed state can be released by releasing the fixing mechanism according to the force from the outer direction applied by nipping both of the right and left wings in the fixed state.

A thirteenth aspect is the intravascular catheter according to the first aspect, wherein the flexible resin member is formed integrally with at least one of the catheter part and a connector part provided on the base end part of the flexible resin member.

A fourteenth aspect is the intravascular catheter according to the first aspect, wherein the catheter part and the flexible resin member are fixed by one of welding, fusion and an adhesive.

A fifteenth aspect is the intravascular catheter according to the first aspect, wherein the flexible resin member is a thermally contractible member, fixed on the catheter part outer surface by thermal contraction.

A sixteenth aspect is the intravascular catheter according to the first aspect, wherein a hub part is provided on the base end side of the flexible resin member.

A seventeenth aspect is the intravascular catheter according to the first aspect, wherein the flexible resin member has a pipe-like shape, whose cross-sectional shape has the ratio A/B of the thickest thick part A and the thinnest thick part B in the range between 1 and 10.

An eighteenth aspect is the intravascular catheter according to the first aspect, wherein the flexible resin member has a pipe-like shape, with an elliptical cross-sectional shape with the ratio C/D of the longer axis C and the shorter axis D in the range between 1 and 4.

DETAILED DESCRIPTION OF THE PREFERRED EMBODIMENTS

Hereinafter an embodiment of the invention will be explained.

The invention provides an intravascular catheter comprising a catheter part and an internal needle disposed through the catheter part, with a flexible resin member disposed at the base end part of the catheter part so as to envelop the catheter outer surface. By pressuring and closing the catheter part via the flexible resin member from the outside with an appropriate tool, the blood leakage can be prevented while preventing breakage of the catheter. Furthermore, a blood leakage prevention means for pressuring and closing the catheter part can be disposed in the intravascular catheter main body in the invention.

The invention will be described in detail with reference to the drawings. The figures referred to just show an example, and thus the invention is not limited thereto.

Figure 1:
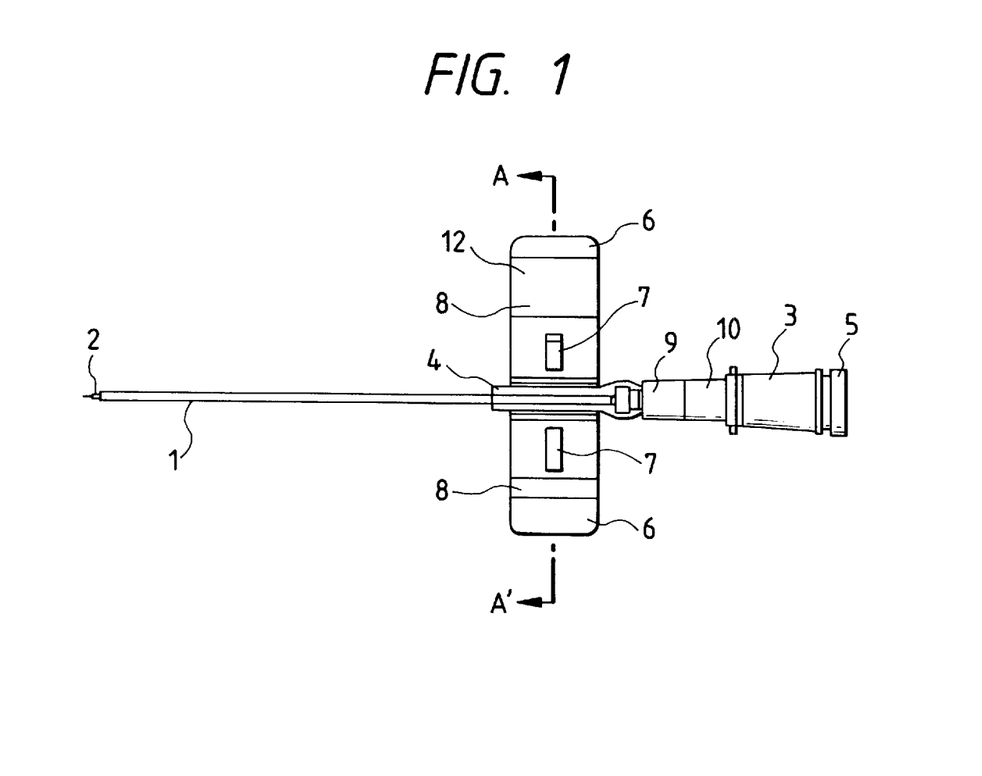
FIG. 1 is a plan view of an intravascular catheter of the type with a pipe-like flexible resin member enveloping the end part of the catheter base according to the invention.
Figure 2:
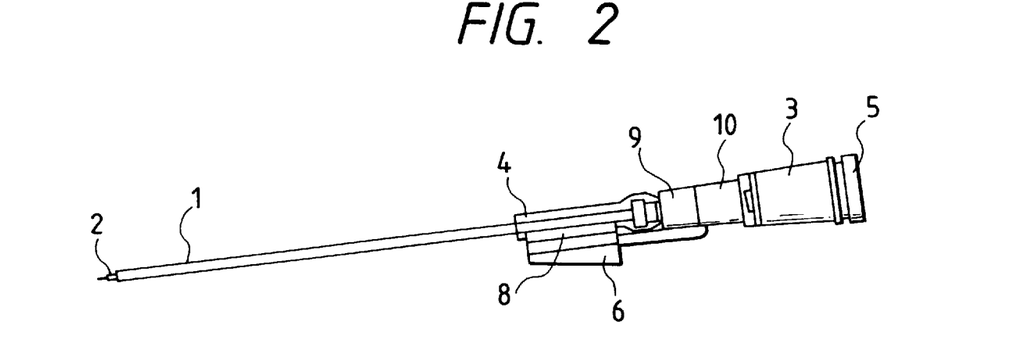
FIG. 2 is a side view of FIG. 1.
Figure 3:
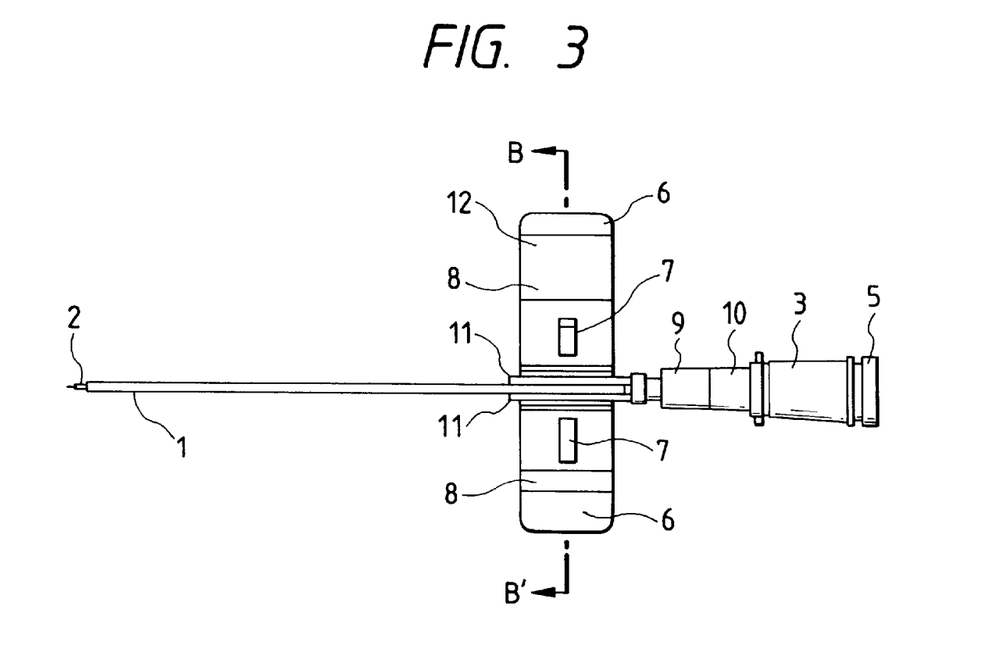
FIG. 3 is a plan view of an intravascular catheter of the type with a plate-like flexible resin member enveloping the right and left outer surface of the catheter base end part according to the invention.
Figure 4:
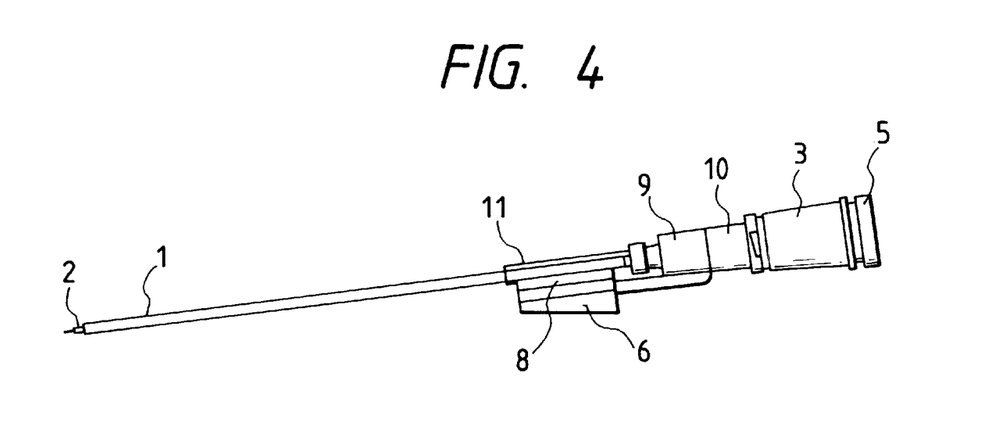
FIG. 4 is a side view of FIG. 3.

As shown in FIGS. 1 and 2, a catheter part 1 and an internal needle 2 disposed therethrough are provided. An internal needle hub 3 is provided at the rear end of the internal needle 2, and a cap 5 containing a blood leakage resistant filter is further disposed on the rear end thereof. A flexible resin member 4 including a reinforcing pipe-like member, capable of alleviating the stress concentration, is provided on the base end part of the catheter 1 so as to envelop the catheter 1 outer surface. In contrast, as shown in FIGS. 3 and 4, a flexible resin member 11 including a reinforcing plate-like member, capable of alleviating the stress concentration, is provided. The position for mounting the flexible resin member onto the catheter is preferably at the catheter base end part. By mounting at the base end part, the part of the catheter inserted and placed in the blood vessel can be longest so that the effect of preventing the bend of the base end part, which is most liable to be bent, can be provided.

Figure 5:
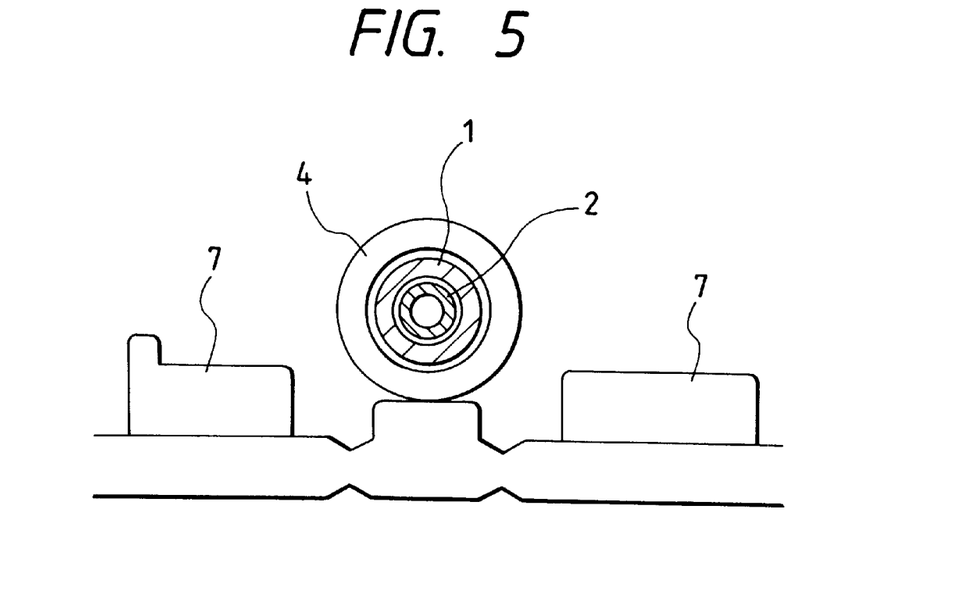
FIG. 5 is an enlarged view of the A–A' cross-section in FIG. 1.
Figure 6:
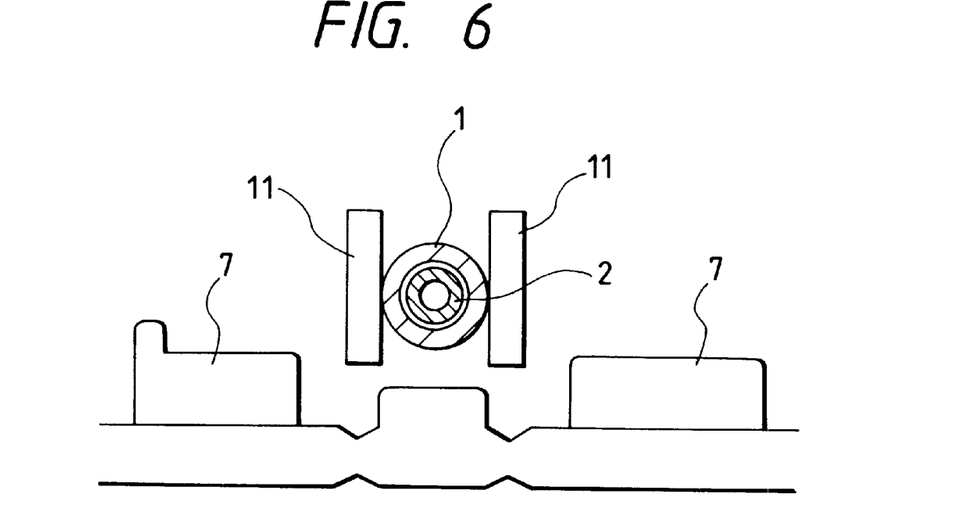
FIG. 6 is an enlarged view of the B–B' cross-section in FIG. 3.

The flexible resin member can adopt any shape as long as it can provide the breakage prevention effect by the stress concentration alleviation, such as the pipe-like member 4 shown in FIGS. 1, 2 and 5 (cross-sectional view taken on the line A–A' in FIG. 1), and the plate-like member 11 shown in FIGS. 3, 4 and 6 (cross-sectional view taken on the line B–B' in FIG. 3). In addition, another example of a flexible resin member is a modified pipe-like member including a slit thereon. Furthermore, other examples include a stripe-like shape, a mesh-like shape, and a line-like shape.

In the invention, the operativity can further be improved by providing a blood leakage prevention means in the catheter main body. Examples of mounting the blood leakage prevention means include a provision of wing parts in the catheter main body, and pressure parts in the wing parts. The wing parts 6 will be explained specifically with reference to drawings.

The wing parts are wing-like parts provided between the catheter part and the connector part on the right and left sides. As shown in FIGS. 1 to 4, the wing parts 6 comprise pressure parts 7. Although the pressure parts 7 provided in the wing parts 6 shown in FIGS. 5 and 6 comprises a projected member, any shape can be adopted as long as it can pressure and close the flexible resin member and the catheter part.

Figure 9:
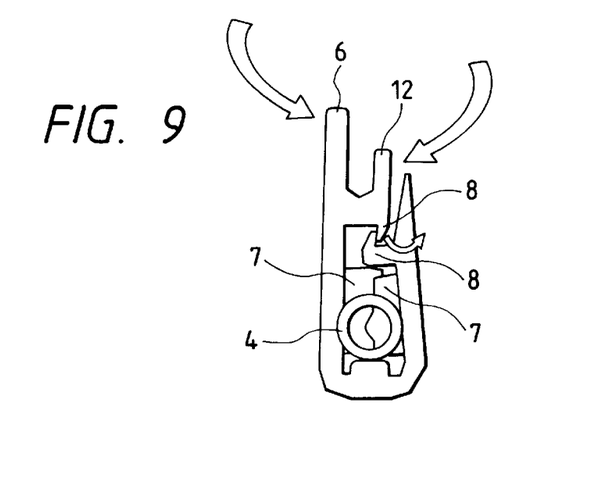
FIG. 9 is a cross-sectional view taken on the line A–A' in FIG. 1, of an embodiment with the fixing mechanism in the pressuring state and the releasing mechanism applied.
Figure 10:
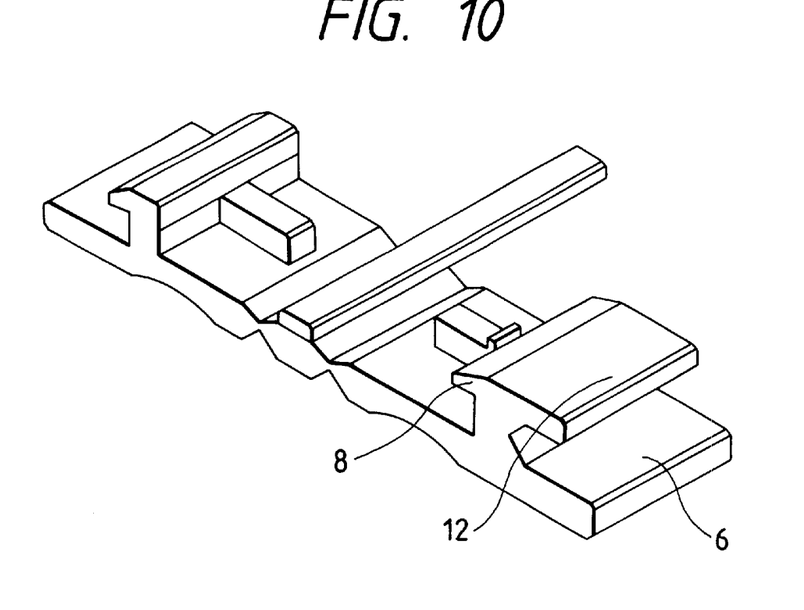
FIG. 10 is a perspective view of an embodiment with a one-touch fixing function applied in the wing parts.

Furthermore, a fixing mechanism as a means for fixing the pressured state as well as a releasing mechanism as a means for releasing the fixed state can further be provided. As the fixing mechanism for the pressured state, any mechanism can be adopted as long as it can fix and maintain the state with the catheter part closed so as to prevent leakage of the blood. Similarly, as the releasing mechanism, any mechanism can be adopted as long as it can release the fixed state. Therefore, they are not particularly limited, but mechanisms capable of easily fixing and maintaining the fixed state as well as capable of easily releasing the state like those shown in FIGS. 9 and 10 are further preferable. In the embodiment shown in FIG. 9, the fixed state can easily be released by nipping a plate-like part 12 provided elongating outside of a nail part of a wing part at one side, and the wing end part 6 so as to lift the nail part. According to the shape, since the fixed state can be set or released by one hand, it is extremely convenient because it cannot prevent the speedy hand of the medical expert. Therefore, although the fixing mechanism and the releasing mechanism can be eliminated, it is more preferable to include them. Although the embodiment shown in FIGS. 9 and 10 includes the fixing mechanism 8 and the releasing mechanism 12, the shape, the mounting position, and the installation method thereof are not particularly limited as long as the wing part can be fixed or released.

Figure 11:
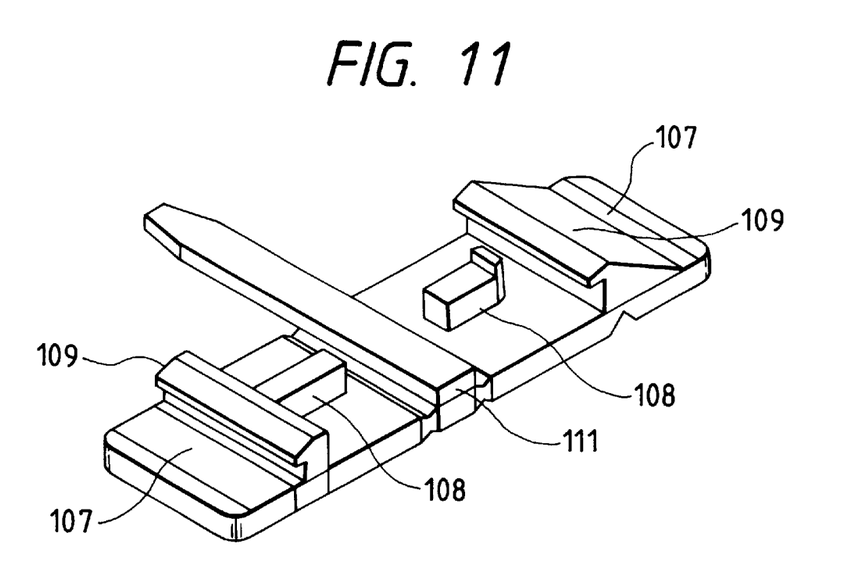
FIG. 11 is a perspective view of another embodiment of the wing parts according to the invention.
Figure 12:
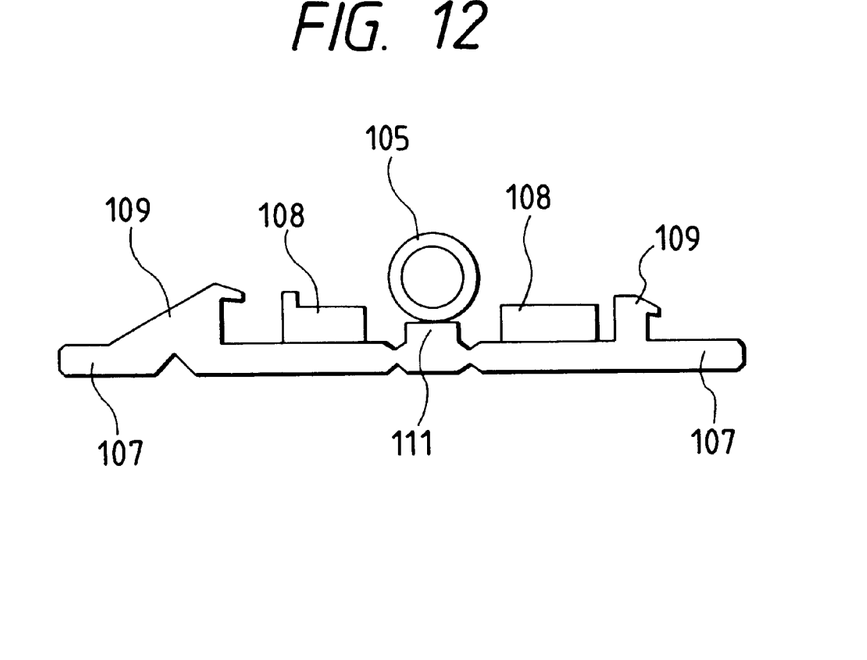
FIG. 12 is a cross-sectional view of another embodiment of the wing parts according to the invention.
Figure 13:
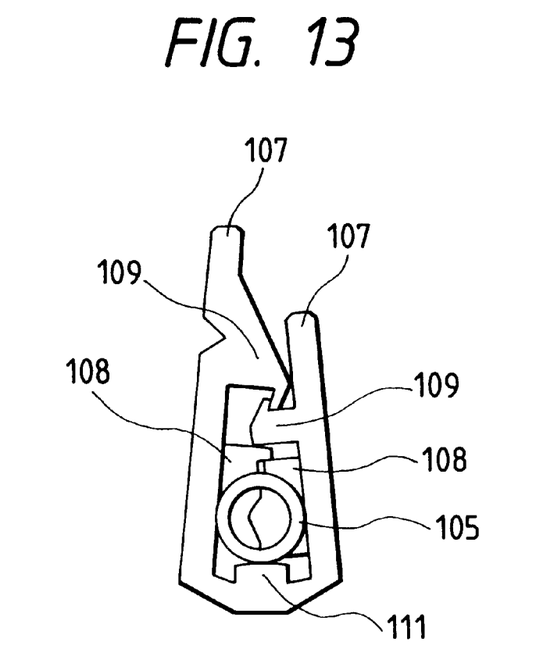
FIG. 13 is a cross-sectional view of another embodiment of the invention, showing the engagement state by a nail of the fixing mechanism.
Figure 14:
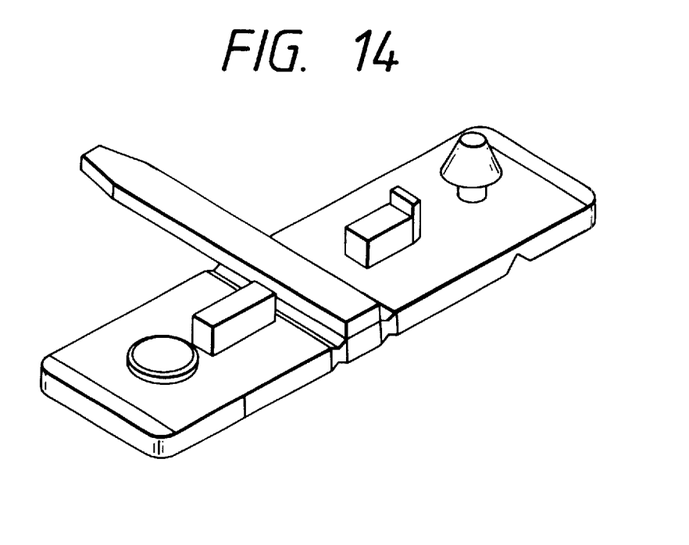
FIG. 14 is a perspective view showing an applied embodiment of the fixing mechanism by fitting the projection and recess parts.
Figure 15:
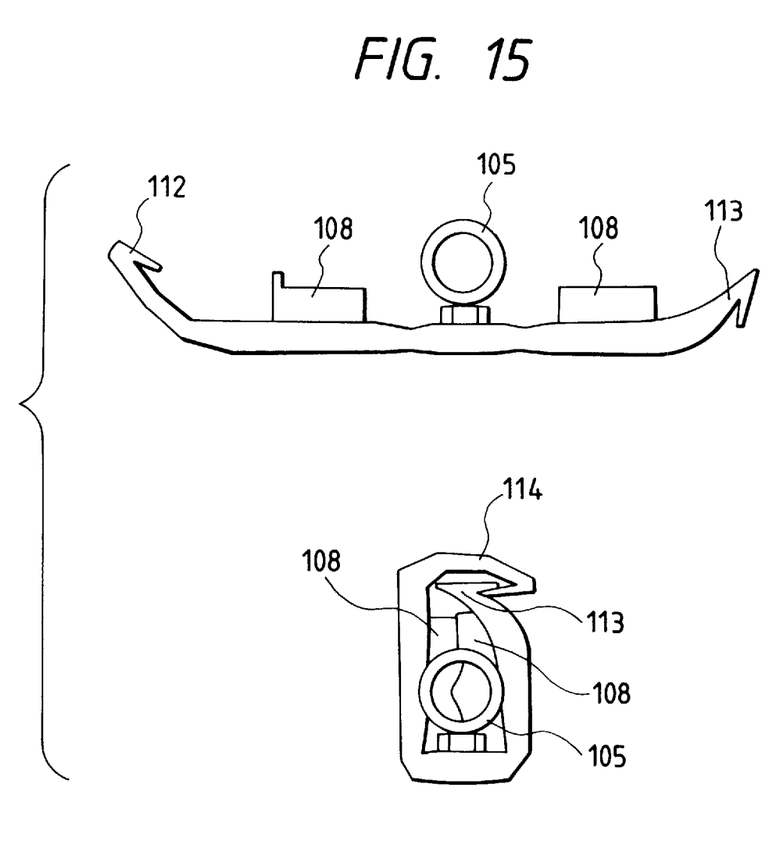
FIG. 15 is a cross-sectional view showing the fixing mechanism of the type with one wing covers the other wing.
Figure 16A:
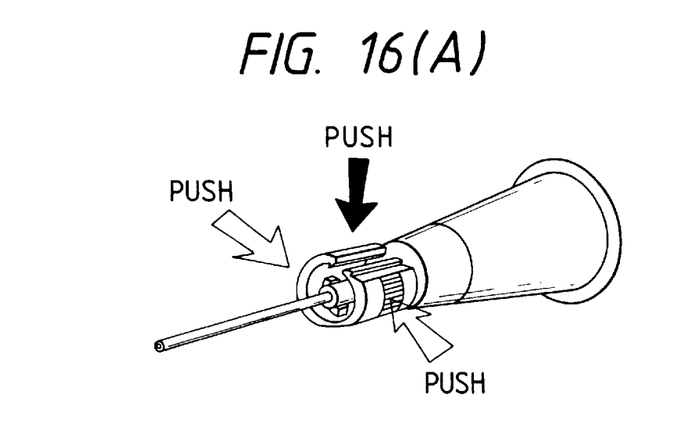
FIGS. 16(A) to 16(D) are perspective views showing the fixed state by the fixing mechanism and the fixation released state using a nail according to another embodiment of the invention.
Figure 16B:
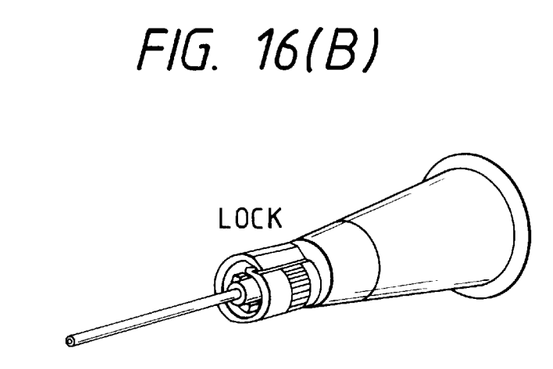
Figure 16C:
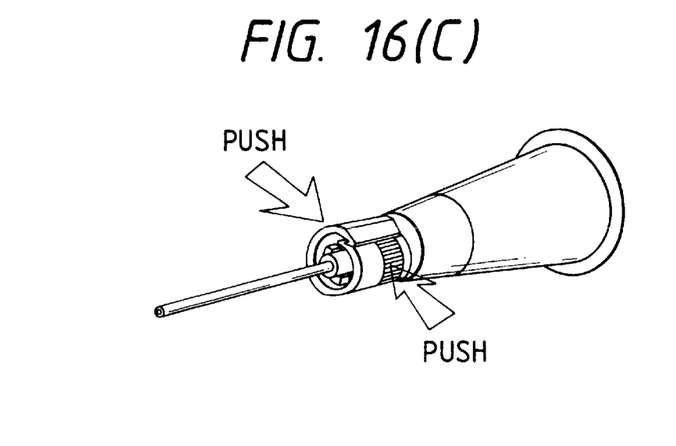
Figure 16D:
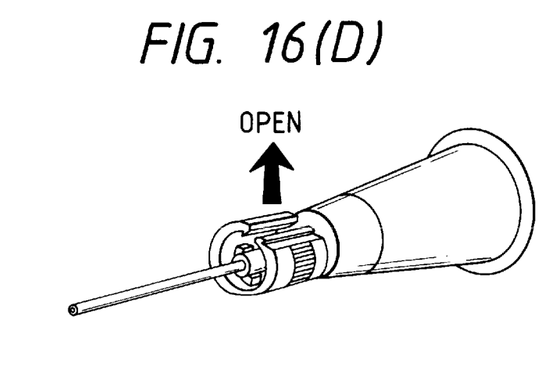

Next, another embodiment of the shape of the wing part will be described. Similar to the wing part shown in FIGS. 9 and 10, wing parts 107 shown in FIGS. 11 to 13 include fixing mechanisms 109 and pressure parts 108. The fixing mechanisms 109 can be in the fixed state according to engagement of nail parts by closing the right and left wings. In the wing parts shown in FIG. 14, a projection-shaped part and a recess-shaped part are provided each on the right and left wings so as to achieve fixation of the closed state by fitting the projection part and the recess part. Moreover, in the wing parts shown in FIG. 15, a method of fixing the closed state by placing a wing 112 on one side over a flexible resin pipe-like member 105 so as to be engaged with a nail part of a wing part 113 on the other side, is adopted. Particularly in this method, in case a material, which is flexible to some extent, is used for the wing material, the fixed state can be maintained easily owing to the shape, even if the wings are curved. Although the shape of the wing parts is developed into a substantially flat plate-like shape at the time of releasing the fixation in the above-mentioned embodiments of the wing parts, a shape of the wing parts with the rolled state maintained without being spread into a substantially flat plate-like shape at the time of releasing fixation can also be adopted as shown in FIGS. 16(A) to 16(D).

Figure 17:
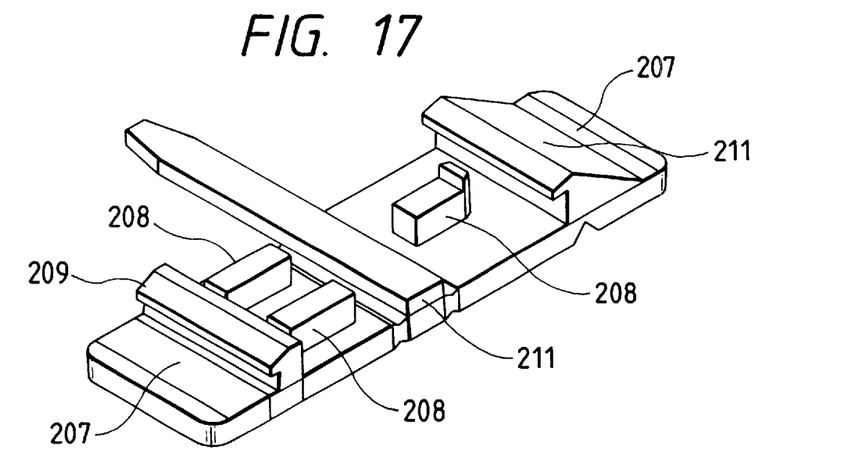
FIG. 17 is a perspective view of the case with the pressure parts provided in three points.
Figure 18:
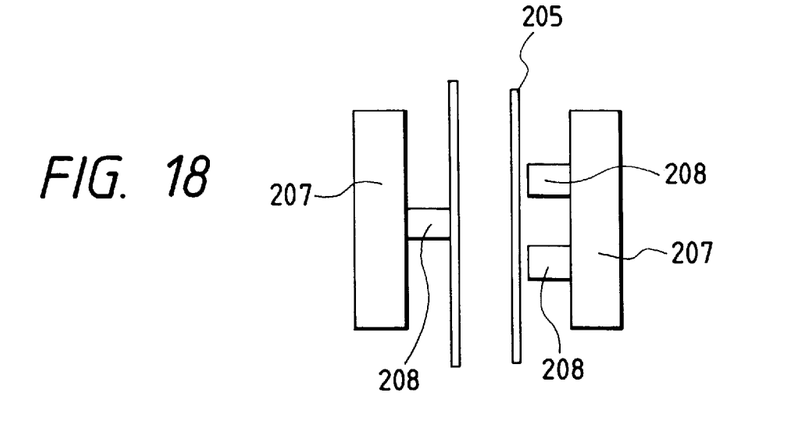
FIGS. 18 and 19 are diagrams showing the state of closing the flexible resin member by bending at three points by the three pressure parts.
Figure 19:
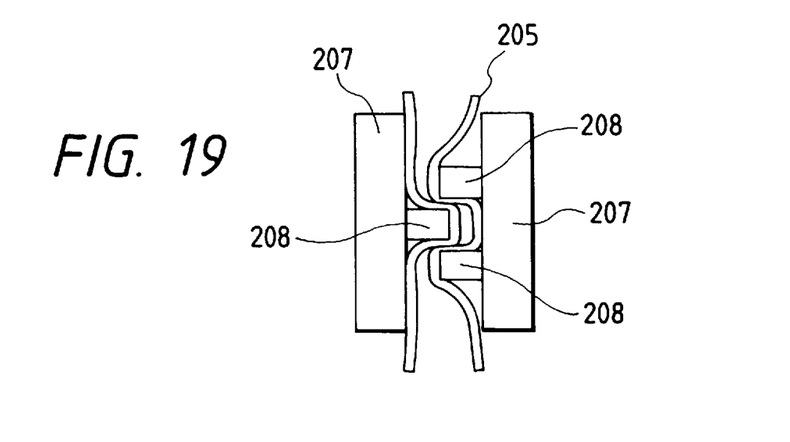
Figure 20:
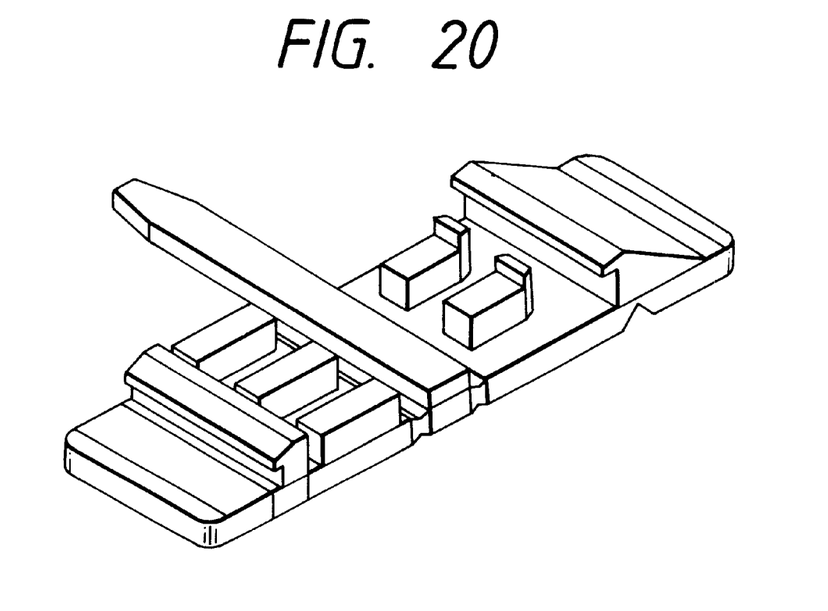
FIGS. 20 and 21 are perspective views of a modified embodiment of the pressure parts on the wings.
Figure 21:
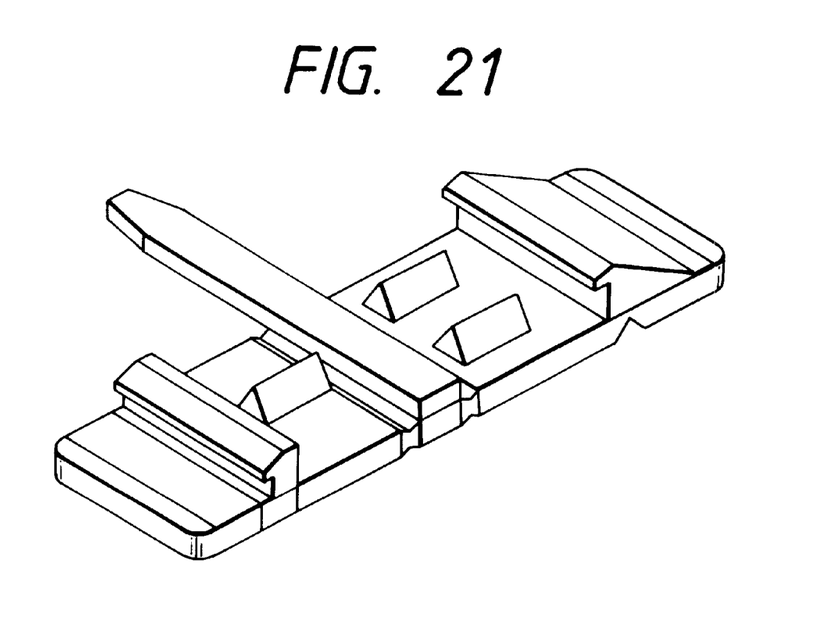

The pressure parts including the wing parts will be explained. The pressure parts are parts for deforming the flexible resin member and the catheter part. For example, they can be projected members including the wing parts, disposed on the right and left wings at symmetrical positions. However, in the case where right and left pressure parts 208 are disposed alternately as shown in FIG. 17, since a flexible resin member 205 can be bent by the pressure parts in the state displaced alternately at the time of closing the wings as shown in FIGS. 18 and 19, the flexible resin member 205 can be closed with a small force, and thus it is effective. Furthermore, as the shape of the pressure parts, the configuration in a plurality as shown in FIG. 20, and a triangular prism shape as shown in FIG. 21 can be conceivable, but the shape is not particularly limited as long as the internal space of the flexible resin pipe-like member 5 can be closed according to the bending operation of the wing parts.

Figure 22:
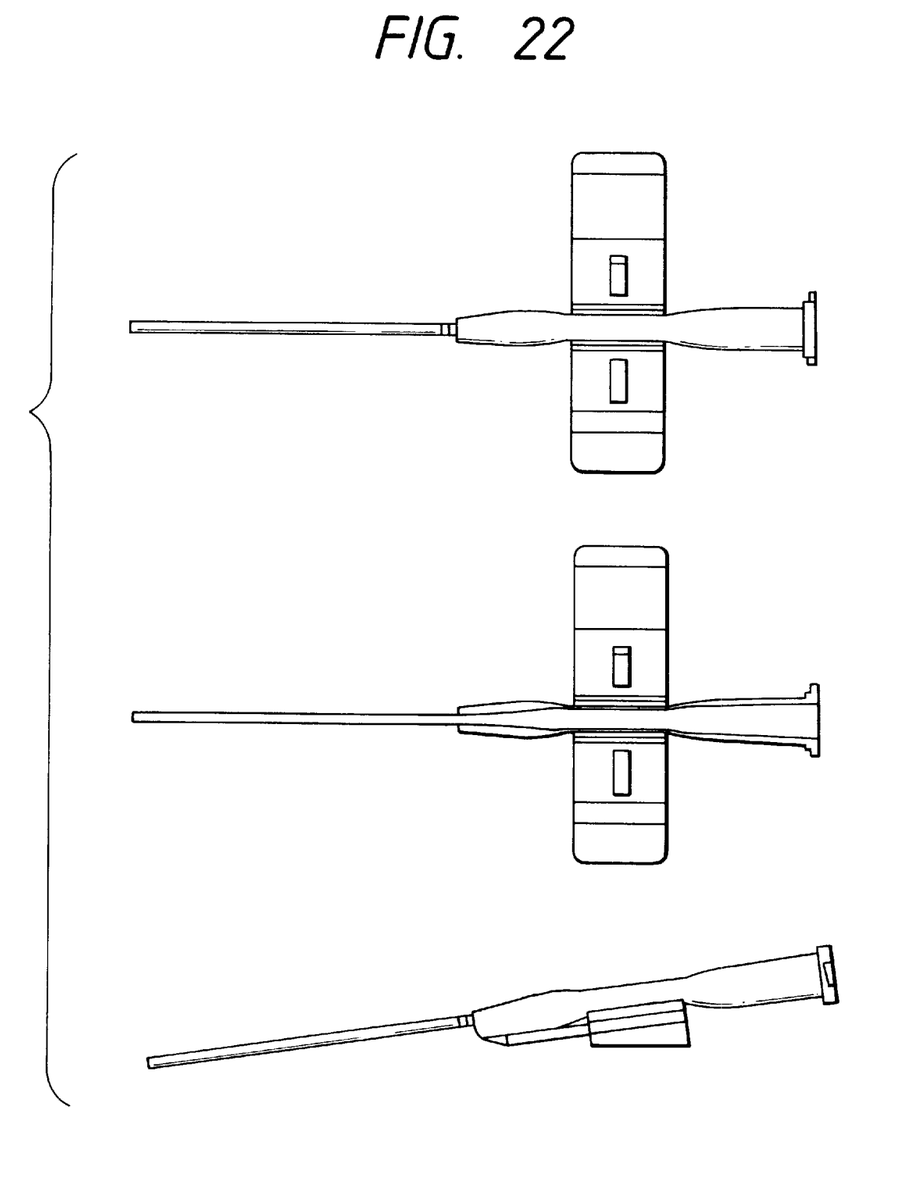
FIG. 22 is a cross-sectional view showing an applied embodiment of integral molding of the hub, wings, and connector.

Furthermore, as shown in FIG. 22, if the flexible resin member is formed integrally with the catheter part or the connector part, since a connection part between the parts can be eliminated, pulling off of the flexible resin member from the catheter part or the connector part can be avoided even if they are dulled by some causes. Moreover, since the gap in the internal space can be reduced, eccentric flow or stagnation can hardly be generated in the blood flow, and thus generation of thrombus can be prevented.

Figure 23A:
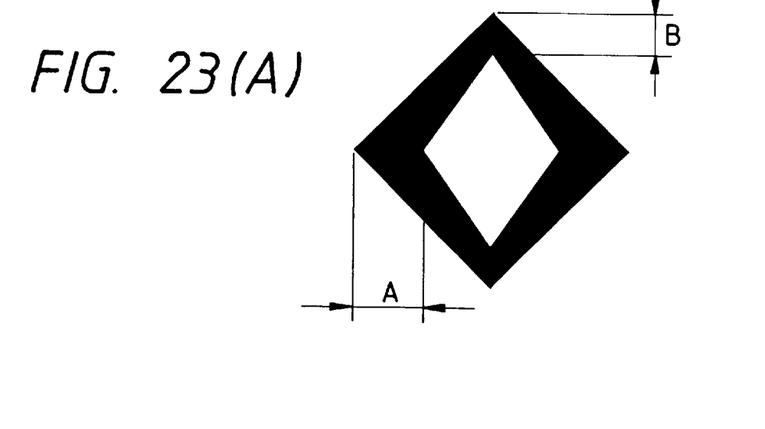
FIGS. 23(A) and 23(B) are cross-sectional views of modified embodiments of the flexible resin pipe-like member.
Figure 23B:
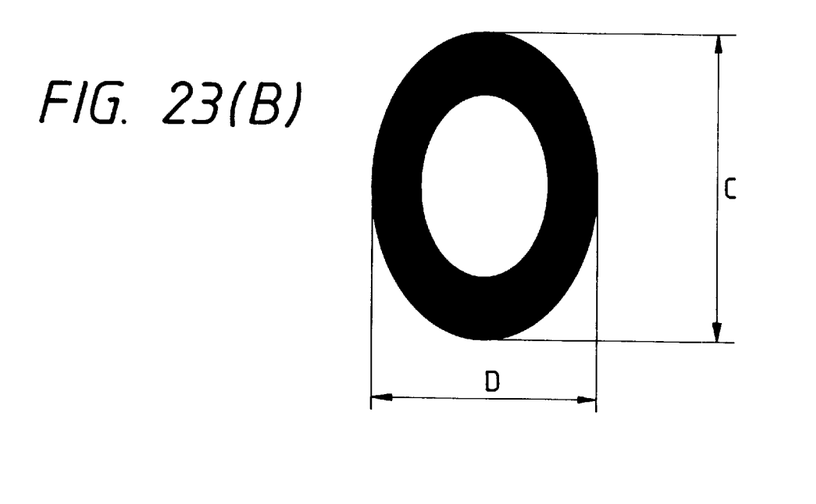

Furthermore, in the case where a pipe-like member is used as the flexible resin member, with a rhomboidal, elliptical, or a flat cross-sectional shape as shown in FIGS. 23(A) and 23(B), closure of the pressure parts can be facilitated, and thus it is further effective. As to the specific range of the shape, in the case of the rhomboidal shape, a ratio A/B of the thickest thick part A and the thinnest thick part B in the range between 1 and 10 is effective. With a smaller ratio, the strength of the thinnest thick part is weak so that the strength of the flexible resin member cannot be maintained;

therefore, it is not preferable. Moreover, in the case of the elliptical cross-sectional shape, a ratio C/D of the longer axis C and the shorter axis D in the range between 1 and 4 is effective. With a larger ratio, the flexible resin member is flattened too much so that the channel is so narrow that the smooth flow of the blood or the transfusion liquid can hardly been ensured; therefore, it is not preferable.

In the invention, a hub part 9 can be disposed at the base end side of the flexible resin member 4, 11 as shown in FIGS. 1 to 4. The hub 9 can be provided either with the same material and continuously with the catheter 1 and the flexible resin member 4 and 11. Furthermore, a connector part 10 is provided at the rear end part of the hub part 9. The connector part can be provided either with the same material and continuously with the hub part 9, but it is more preferable that it is provided continuously therewith. The hub part is a part for bonding the catheter part and the connector part, and the connector part is a part for connecting the intravascular catheter and an external transfusion liquid circuit. Compared with the conventional intravascular catheter including the components in the order of the hub part, the flexible resin member, and the connector part, the intravascular catheter according to the invention including the components in the order of the flexible resin member, the hub part, and the connector part can achieve integration of the hub part and the connector part provided adjacently because the flexible resin member is provided onward with respect to the hub part so that the number of parts can be reduced so as to achieve the compactness as well as the operativity and the handling convenience can further be improved.

As the part for connecting the wing parts 6 to the catheter part, the hub part 9 can preferably adopted as shown in FIGS. 1 to 4, but it is not limited thereto. That is, it can be the catheter part 1, the flexible resin member 4, 11, or the like, and thus it is not particularly limited as long as it can be fixed to the main body.

Hereinafter the operation method of the intravascular catheter will be explained.

Figure 7:
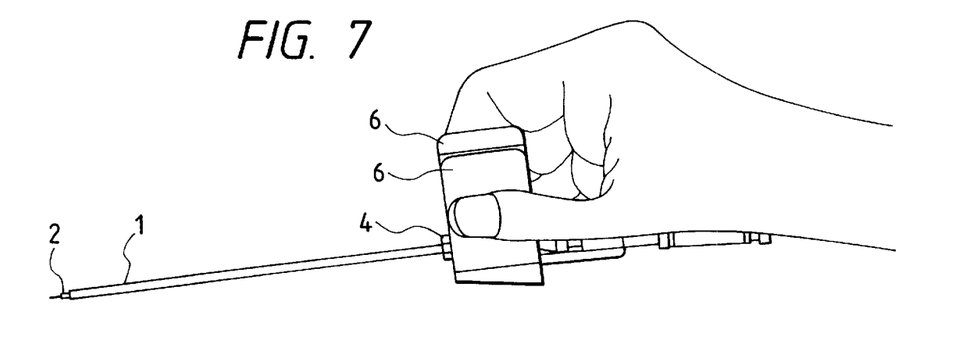
FIG. 7 is an diagram showing the operation state at the time of piercing an intravascular catheter according to the invention.
Figure 8:
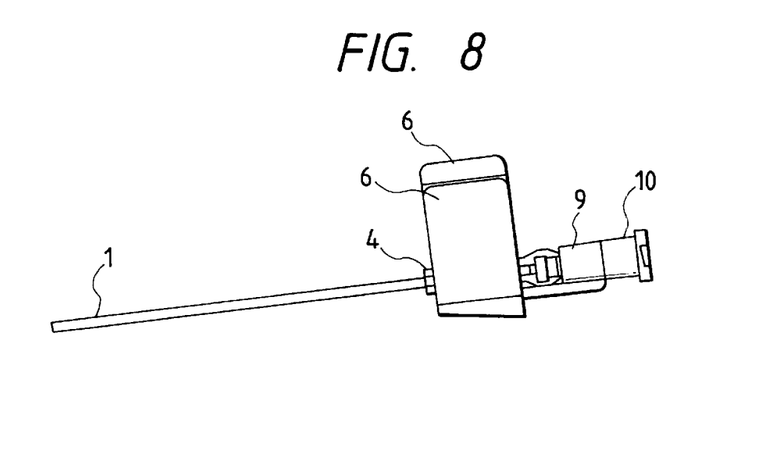
FIG. 8 is a diagram showing the state of pressuring a flexible resin pipe-like member by the wing parts, and fixing and maintaining the pressured and closed state by the fixing mechanism after taking out the internal needle of the intravascular needle according to the invention.

As shown in FIGS. 7 and 8, with both wing parts 6 bent upward, the wing lower surfaces are nipped by fingers so as to have the flexible resin member 4, the end part of the catheter 1, and the internal needle 2 in the state gripped by the pressure parts 7 on both wings.

Thereafter, the tip end of the internal needle 2 is pierced into the blood vessel. With the internal needle 2 serving as the guide, the catheter 1 is inserted into the blood vessel. Insertion of the internal needle 2 into the blood vessel can be confirmed by flow-out of the blood through the internal needle 2 from the rear end of the internal needle of the internal hub 3. Moreover, leakage of the blood flown out to the outside can be prevented by a blood leakage resistant filter of a cap 5 provided at the rear end of the internal hub 3.

After insertion of the catheter 1 into the blood vessel, the internal needle 2 is taken out from the blood vessel and the catheter 1. In this case, pressure on the wing parts 6 by fingers is released slightly for facilitating the pull-out of the internal needle 2.

Pressure on the wings 6 by fingers is increased immediately after pulling out the internal needle 2 so that the tip end thereof passes by the wing parts 6 so as to pressure and close the flexible resin member 4, and the end part of the catheter 1 so that blood leakage from the blood vessel out of the connector part 9 via the catheter can completely be prevented. Furthermore, since the closed state can be maintained owing to the fixing mechanism 8, the operator can concentrate on the operation for abandoning the pulled-out internal needle as well as the subsequent operation of connecting the connector part 9 with the external circuit such as a medicine liquid and a transfusion liquid can be executed with both hands.

After connecting the connector part 9 with the external circuit, the pressured and closed state can be released by releasing the pressure by the fingers or releasing the fixed state by the releasing mechanism 12 in the case where it is fixed by the fixing mechanism 8 so that the wing parts 6 are spread in the initial state so as to fix the wing parts 6 onto the skin surface with a tape.

As an applied embodiment, the invention can be applied in an intravenous needle, an intra-arterial needle, and a dialyzing needle. Furthermore, it can be applied in an introducer kit and an IVH catheter kit, but it is not limited thereto.

Figure 24:
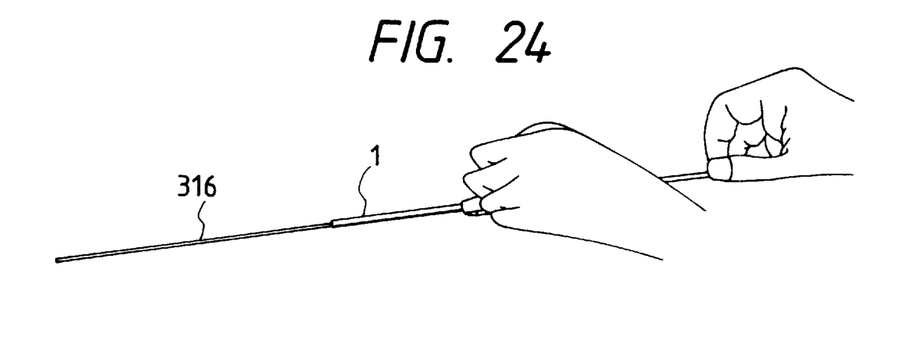
FIG. 24 is a plan view showing an applied embodiment of the invention to an introducer kit.

An embodiment of the operation method as the introducer kit will be described with reference to FIGS. 1, 8, and 24. With the internal needle 2 inserted as shown in FIG. 1, the wing parts 6 are nipped by fingers for inserting the catheter into the blood vessel with the flexible resin member 4 and the internal needle 2 gripped by the pressure parts 7. After pulling out the internal needle, the wing parts 6 are further pressured so as to close the flexible resin member 4. By fixing the closed state by the fixing mechanism 8 so as to be in the state of FIG. 8, the blood leakage is restrained. Furthermore, at the time of introducing an external catheter such as a guide wire 316, after releasing the fixing mechanism 8, the guide wire 316 is introduced with the pressure by the pressure parts gradually released by fingers of one hand. By further inserting the guide wire while further increasing the pressure by fingers at the time the guide wire 316 passes by the pressure parts 7 so as to grip the flexible resin member 4 and the guide wire 316 by the pressure parts, the guide wire 316 can be introduced into the blood vessel while restraining the blood leakage due to backward flow from the blood vessel as shown in FIG. 24.

The materials used in the invention will be explained.

As the material for the catheter part, thermoplastic resins such as fluorine resins, urethane resins, nylon resins, polyester resins, polyethylenes, and polypropylenes are preferable, but it is not limited thereto.

Moreover, the flexible resin member can be made from the same material as the catheter part and the hub part. Furthermore, it can be provided continuously with the hub part. As the material therefor, flexible resins, such as olefin based elastomers including 1,2-polybutadiene, styrene-based elastomers, urethane resins, polyethylenes, polypropylenes, nylon resins, silicone resins, polyvinyl chloride resins, natural rubbers, and mixtures thereof can be used. Since butyl rubbers and urethane resins can easily alleviate the stress concentrated on the pressure parts, they are preferable for the capability of preventing breakage of the catheter in the pressured and closed state further effectively, but it is not limited thereto.

In the case urethane resins are used for the materials of both catheter part and flexible resin member, by using a urethane resin having a higher elasticity for the flexible resin member compared with that of the catheter part, release of the pressured and closed state by the fixing mechanism part can be executed smoothly.

As the material for the wing parts, flexible resins, that is, the materials same as that of the flexible resin member, the hub part, and the connector part can be used. Examples thereof include olefin-based elastomers including 1,2-polybutadiene, styrene-based elastomers, urethane resins, polyethylenes, polypropylenes, nylon resins, silicone resins, polyvinyl chloride resins, natural rubbers, and mixtures thereof, but it is not limited thereto.

As the material for the pressure parts, the fixing mechanism part, and the releasing mechanism part, both elastic materials and non-elastic materials can be used. Furthermore, it can either be same as or different form the material of the wing parts. Examples of the elastic materials include olefin-based elastomers including 1,2-polybutadiene, styrene-based elastomers, urethane resins, polyethylenes, polypropylenes, nylon resins, silicone resins, polyvinyl chloride resins, natural rubbers, and mixtures thereof, but it is not limited thereto. Examples of the non-elastic materials include engineering plastics such as polysulfones, polyether sulfones, polycarbonates, and polyimides, but it is not limited thereto. For example, as other non-elastic materials, metals or alloys such as iron, silver, copper, aluminum and stainless steel can also be used.

Although the hub part is a part for connecting the catheter part with the connector part, it can be provided continuously with the catheter part or the flexible resin part. The material thereof can be flexible resins, that is, the materials same as that of the flexible resin member. Examples thereof include olefin-based elastomers including 1,2-poly butadiene, styrene-based elastomers, urethane resins, polyethylenes, polypropylenes, nylon resins, silicone resins, polyvinyl chloride resins, natural rubbers, and mixtures thereof, but it is not limited thereto.

Although the connector part is a part for connecting with the liquid circuit for a medicine liquid or a transfusion liquid, it can be provided continuously with the hub part. The material thereof can be flexible resins, that is, the materials same as that of the flexible resin member. Examples thereof include olefin-based elastomers including 1,2-polybutadiene, styrene-based elastomers, urethane resins, polyethylenes, polypropylenes, nylon resins, silicone resins, polyvinyl chloride resins, natural rubbers, and mixtures thereof, but it is not limited thereto.

As a method for bonding the catheter part 1 and the flexible resin member, a method of injecting an adhesive into a gap part between the outer surface of the catheter part and the inner surface of the flexible resin member, and curing can be presented. As another example, a method of preliminarily applying an adhesive on the outer surface of the catheter part, placing the flexible resin member thereon, and curing can be presented. It is further preferable to use a photo-curing adhesive, and a method of directing a radioactive ray from an opening part or from the outside for curing can be presented, but it is not limited thereto. Moreover, it is also possible to achieve fusion or adhesion by thermal fusion, high frequency induction heating, or high frequency dielectric heating. Since the circuit restoration force after being released from the closed state is improved in this case, it is further preferable.

Furthermore, in the case where the catheter part and the flexible resin member are made of the same material, adhesion using an organic solvent is also possible. For example, in the case where a urethane resin is used for the material of the catheter part and the flexible resin member, adhesion can be completed by dropping a few drops of an organic solvent; therefore, the operation can be simple.

Moreover, as the flexible resin member, a member made from a thermally contractible material can be used. A method of placing a thermally contractible member having an inner diameter larger than the catheter outer diameter on the catheter outer surface, and causing the thermal contraction in an oven or by a drier for fixation on the catheter outer surface can be presented. Since the method is simpler than the method using an adhesion or thermal fusion, it is further preferable, but it is not limited thereto. Examples of the thermally contractible member include thermally contractible members having the elasticity, such as those containing an olefin resin, a polyvinyl chloride resin, and a silicone resin, but it is not limited thereto.

Hereinafter the invention will be explained with reference to specific examples, but the invention is not limited to these examples.

In FIG. 1, the catheter part 1 is produced by extrusion molding from, for example, a urethane resin into a flexible tube member having a outer diameter of 0.3 to 20 mm and a thickness of 0.08 to 5 mm, with the inner diameter thereof slightly larger than the outer diameter of the blood vessel piercing internal needle 2 to be introduced therein, and the base end thereof connected with the hub part 9. As shown in FIG. 1, the hub part 9 produced by injection molding from, for example, 1,2-polybutadiene, is fitted with the flexible resin member 4. The flexible resin member 4 is produced by extrusion molding or injection molding from, for example, 1,2-polybutadiene. Since the blood flow amount differs depending on the application position, such as for dialysis, artery, vein, or introducer kit, the size of the flexible resin member 4 and the wing parts 6 is changed accordingly. For example, an outer diameter of 1.0 to 40 mm, a thickness of 0.08 to 10 mm, and a length of 3 to 100 mm can be adopted. Furthermore, an outer diameter of 1.2 to 30 mm, a thickness of 0.1 to 8 mm, and a length of 5.0 to 80 mm are further preferable. A pair of the flexible wings 6 produced by injection molding from a polyethylene elongate symmetrically on both right and left ends of the flexible resin member 4 in the direction substantially orthogonal to the axial direction of the catheter. The width of the wing parts 6 is 2 to 80 mm, and the length from the main body side to the end part is 5 to 100 mm. It is further preferable that the wing width is 3 to 70 mm, and the length from the main body side to the end part is 8 to 80 mm. The pressure parts 7 are formed preferably integrally with the wing parts on the upper surface of the wing parts 6. The height of the pressure parts is 0.8 to 50 mm, and is further preferably 1.0 to 40 mm.

As heretofore described, since the flexible resin member including a reinforcing pipe-like member or a plate-like member capable of alleviating stress concentration is provided in the catheter part for pressuring and closing the catheter part therefrom, the stress can be alleviated compared with the conventional case of directly pressuring and closing the catheter part so that blood leakage can be prevented without generating breakage or cut-off of the catheter.

Furthermore, since the pressure parts are provided for pressuring and closing via the flexible resin member, breakage or cut-off of the catheter according to the excessive pressure by metal forceps in the conventional method can be restrained. Moreover, since the pressure parts are provided in the intravascular catheter main body, an extra closing device needs not be prepared as well as the operation of taking out the internal needle is facilitated compared with the conventional method.

Furthermore, since the fixing mechanism capable of fixing the pressured state is provided, freedom of use of both hands necessary in the subsequent operation of connecting the external circuit such as a medicine liquid and a transfusion liquid is ensured. Moreover, since the releasing mechanism capable of easily releasing the fixed state is provided, the fixed state can be released without giving a pain to the patient. Since the pressure parts, the fixing mechanism and the releasing mechanism are provided integrally with the wing parts, a compact configuration, a good operativity, and improved economy and productivity can be achieved without giving a pain to the patient at the time of closing the catheter by pressing thereto as in the conventional method.

Furthermore, since the hub part is provided at the base end side of the flexible resin member, the flexible resin member needs not be disposed between the hub part and the connector part so that the hub part and the connector part are provided adjacently for allowing the integration. Accordingly, the number of parts is reduced so that the productivity and economy are improved as well as the entire length is shortened to achieve the compactness and improve the handling convenience.

Moreover, since the flexible resin member is bonded with the catheter part, the catheter restoration force after being released from the pressured and closed state can be improved. Furthermore, in the case where the flexible resin member is made from a thermally contractible material, it can be fixed on the outer surface of the catheter without the need of using an adhesive.

Furthermore, even in the case where the catheter is used as the introducer kit for introducing an external catheter such as a guide wire, blood leakage after taking out the internal needle can be prevented as well as, since the wing parts can be fixed and maintained in the closed state, blood leakage can be restrained at the time of introducing the external catheter such as a guide wire by nipping the wing parts for pressuring the flexible resin pipe-like member.

What is claimed is:

1. An intravascular catheter comprising:

a catheter part;

an internal needle disposed through the catheter part;

a flexible resin member disposed on the outer surface of the catheter part; and a blood leakage preventing member for preventing leakage of blood by closing the catheter part via the flexible resin member;

wherein the blood leakage prevention member includes a pressure part capable of pressuring the catheter part via the flexible resin member;

wherein the blood leakage prevention member includes a fixing mechanism capable of fixing the pressure part in the pressuring state and a releasing mechanism capable of releasing the pressuring state of the pressure part; and wherein the blood leakage prevention member comprises wing parts disposed on the right and left sides with respect to the axial direction of the catheter part, the wing parts being provided integrally with at least one of the pressure part capable of pressuring the catheter part via the flexible resin member, the fixing mechanism capable of fixing the pressure part in the pressuring state, and the releasing mechanism capable of releasing the pressuring state of the pressure part.

2. The intravascular catheter according to claim 1, wherein the fixing mechanism is a nail part provided on at least one of the right and left wings, and is fixable by engagement with the other side wing part.

3. The intravascular catheter according to claim 1, wherein the fixing mechanism is a nail part provided on at least one of the right and left wings, and the fixed state by engagement with the other side wing part is capable of being released.

4. The intravascular catheter according to claim 1, wherein the fixing mechanism is a pair of projection and recess fitting parts provided respectively on the right and left wings, and is fixable by engagement of the projection and recess of the fitting parts.

5. The intravascular catheter according to claim 1, wherein the fixing mechanism achieves fixation by engagement of the right and left wings such that one of them covers the other.

6. The intravascular catheter according to claim 5, wherein the fixed state can be released by releasing the fixing mechanism according to the force from the outer direction applied by nipping both of the right and left wings in the fixed state.

7. The intravascular catheter according to claim 1, wherein the flexible resin member is formed integrally with at least one of the catheter part and a connector part provided on the base end part of the flexible resin member.

8. The intravascular catheter according to claim 1, wherein the catheter part and the flexible resin member are fixed by one of welding, fusion and an adhesive.

9. The intravascular catheter according to claim 1, wherein the flexible resin member is a thermally contractible member, fixed on the catheter part outer surface according to thermal contraction.

10. The intravascular catheter according to claim 1, wherein a hub part is provided on the base end side of the flexible resin member.

11. The intravascular catheter according to claim 1, wherein the flexible resin member has a pipe-like shape, whose cross-sectional shape has the ratio A/B of the thickest thick part A and the thinnest thick part B in the range between 1 and 10.

12. The intravascular catheter according to claim 1, wherein the flexible resin member has a pipe-like shape, with an elliptical cross-sectional shape with the ratio C/D of the longer axis C and the shorter axis D in the range between 1 and 4.

* * * * *